(12) United States Patent
Lassetter et al.

(10) Patent No.: US 8,095,386 B2
(45) Date of Patent: Jan. 10, 2012

(54) SYSTEM AND METHOD FOR USING AND MAINTAINING A MASTER MATCHING INDEX

(75) Inventors: James K. Lassetter, Park City, UT (US); David Coyle, Sandy, UT (US); Jared Crapo, Sandy, UT (US)

(73) Assignee: Medicity, Inc., Salt Lake City, UT (US)

( * ) Notice: Subject to any disclaimer, the term of this patent is extended or adjusted under 35 U.S.C. 154(b) by 1005 days.

(21) Appl. No.: 11/416,666

(22) Filed: May 2, 2006

(65) Prior Publication Data

US 2006/0271401 A1   Nov. 30, 2006

Related U.S. Application Data

(60) Provisional application No. 60/677,754, filed on May 3, 2005.

(51) Int. Cl.
*G06Q 50/00* (2006.01)
*G06F 17/30* (2006.01)

(52) U.S. Cl. ............ 705/3; 707/760; 707/761; 707/762; 705/2

(58) Field of Classification Search ............... 707/1–10, 707/760, 762–763, 761; 713/2–21; 705/2, 705/3
See application file for complete search history.

(56) References Cited

U.S. PATENT DOCUMENTS

| | | | | |
|---|---|---|---|---|
| 5,418,943 | A * | 5/1995 | Borgida et al. | 707/4 |
| 6,304,864 | B1 * | 10/2001 | Liddy et al. | 706/15 |
| 6,321,224 | B1 * | 11/2001 | Beall et al. | 1/1 |
| 6,324,534 | B1 * | 11/2001 | Neal et al. | 707/3 |
| 6,751,630 | B1 * | 6/2004 | Franks et al. | 707/102 |
| 7,379,885 | B1 * | 5/2008 | Zakim | 705/2 |
| 2002/0007285 | A1 * | 1/2002 | Rappaport | 705/2 |
| 2002/0010679 | A1 * | 1/2002 | Felsher | 705/51 |
| 2002/0103876 | A1 * | 8/2002 | Chatani et al. | 709/217 |
| 2002/0107992 | A1 * | 8/2002 | Osbourne et al. | 709/310 |
| 2003/0126120 | A1 * | 7/2003 | Faybishenko et al. | 707/3 |
| 2003/0182282 | A1 * | 9/2003 | Ripley | 707/5 |
| 2003/0212676 | A1 * | 11/2003 | Bruce et al. | 707/5 |
| 2004/0015485 | A1 * | 1/2004 | Salerno et al. | 707/3 |
| 2004/0030682 | A1 * | 2/2004 | Porter et al. | 707/3 |
| 2004/0122707 | A1 | 6/2004 | Sabol et al. | |
| 2004/0260577 | A1 * | 12/2004 | Dahlin et al. | 705/2 |
| 2004/0267729 | A1 | 12/2004 | Swaminathan et al. | |
| 2005/0033730 | A1 | 2/2005 | Chaudhuri et al. | |
| 2005/0091106 | A1 | 4/2005 | Reller et al. | |
| 2005/0160083 | A1 * | 7/2005 | Robinson | 707/3 |

OTHER PUBLICATIONS

PCT International Search Report and Written Opinion, PCT/US06/17189, Sep. 28, 2007, 7 pages.

* cited by examiner

*Primary Examiner* — Kambiz Zand
*Assistant Examiner* — Michael Guirguis
(74) *Attorney, Agent, or Firm* — Patent Law Works LLP (57) ABSTRACT

A master matching index (MMI) is accessible to a plurality of entities connected over a network. Access to the MMI is provided via MMI adapters distributed among the entities. A distributed MMI adapter contains matching algorithms that specify how record queries from its associated entity should be compared against information in the MMI. Accordingly, an MMI may be searched for matches according to matching algorithms specified by disparate entities.

29 Claims, 4 Drawing Sheets

SYSTEM AND METHOD FOR USING AND MAINTAINING A MASTER MATCHING INDEX

CROSS-REFERENCE TO RELATED APPLICATIONS

The present application is based on and claims benefit under 35 U.S.C. §119(e) of U.S. Provisional Patent Application No. 60/677,754, filed on May 3, 2005 and entitled "A System and Method for Using and Maintaining a Distributed Master Patient Index", the entirety of which is hereby incorporated by reference.

BACKGROUND

Providing quality health care and related services (e.g., pharmaceutical services, veterinary services) depends on having the ability to reliably access various types of records. In the case of patients, information regarding a particular patient may be needed by various different types of health care related entities. For example, any one of a hospital, a health care organization, a clinic, a clinical or hospital lab, an insurance company, or a pharmacy may need access to particular computerized patient information. Such information retrieval generally occurs by querying a database associated with the health care related entity performing the query. The database typically contains all or part of what is referred to as a "Master Patient Index" (MPI), which is a collection of patient information and identifiers. Particularly, an MPI is a collection of indexed patient records, where each record contains information about a particular patient. In practice, user-level applications submit known or believed patient information to the database, which then uses the MPI to match the incoming data with information stored in the database. If a match is found, the record (or pointer thereto) is returned to the querying entity. If the patient cannot be matched, the MPI creates a new patient record.

While a typical MPI is designed to work within or for a particular health care related entity (e.g., a single hospital, a medical group), including among disparate information systems across the health care related entity, the increased mobility of individuals throughout the overall health care system and the constant evolution of health care in general requires that patient information be reliably accessible by a local, state, regional, or national community of health care related entities. Reaching this goal is further complicated by the presence of political issues among entities and the lack of cooperation between competing entities.

One possible way to achieve community-wide access is to use a centralized MPI, whereby separate health care related entities would patient match using the same centralized MPI. However, such a centralized MPI may prove to be flawed, or at least non-optimal, in view of the fact that different health care related entities have different ways of configuring, submitting, searching for, and handling patient information. For example, one health care related entity could have policies in place or be configured to enter all '1's in a social security field of a query when the social security number of a patient is unknown, whereas another health care related entity could have policies in place or be configured to enter '123-45-6789' for an unknown social security number. Thus, when configuring the centralized MPI, algorithm adjustments aimed to improve a matching accuracy for one health care related entity could come at the expense of reducing matching accuracy for another health care related entity. Accordingly, because of such a "win/loss" effect, otherwise potential benefits of using a centralized MPI are compromised.

Another way to "share" patient information involves the use of an electronic data interchange (EDI). EDI allows entities to transfer data according to prescribed business standards. However, although EDI can be used to share patient information, EDI is not helpful for determining the identity of a patient based on incomplete or ambiguous information. In other words, EDI poorly supports, if at all, reliably matching queries with patient records.

SUMMARY

According to at least one aspect of one or more embodiments of the present invention, a system for accessing a master matching index (MMI) is described. The system includes an MMI services unit operatively coupled to the MMI and arranged to control access to the MMI. The system also includes an MMI adapter operatively coupled to the MMI services unit, where the MMI adapter is accessible to a secondary system. The MMI services unit is further arranged to receive a query initiated by the secondary system and attempt to match the query to information in the MMI according to a matching algorithm specified by the MMI adapter.

According to at least one other aspect of one or more embodiments of the present invention, a method comprises: accessing a user interface supported by a master matching index (MMI) adapter operatively coupled to an MMI; specifying a query for a record via the user interface; and comparing the query against information in the MMI according to a matching algorithm specified in the MMI adapter.

According to at least one other aspect of one or more embodiments of the present invention, a method for matching information in a master matching index (MMI) is described. The method includes receiving a query from an entity via an MMI adapter and attempting to match the query with a record indexed in the MMI according to a matching algorithm specified in the MMI adapter.

According to at least one other aspect of one or more embodiments of the present invention, a method is described for passing patient information over a network having at least first and second health care related entities. The method includes storing patient information in a master patient index (MPI). The method also includes receiving a first query from the first health care related entity for patient information in the MPI, where a first MPI matching algorithm for the first query is specific to the first health care related entity. The method further includes receiving a second query from the second health care related entity for patient information in the MPI, where a second MPI matching algorithm for the second query is specific to the second health care related entity. Performance of the first MPI matching algorithm and performance of the second MPI matching algorithm are independent of one another.

The features and advantages described herein are not all inclusive, and, in particular, many additional features and advantages will be apparent to those skilled in the art in view of the following description. Moreover, it should be noted that the language used herein has been principally selected for readability and instructional purposes and may not have been selected to circumscribe the present invention.

BRIEF DESCRIPTION OF DRAWINGS

Each of the figures referenced above depict an embodiment of the present invention for purposes of illustration only. Those skilled in the art will readily recognize from the following description that one or more other embodiments of the structures, methods, and systems illustrated herein may be used without departing from the principles of the present invention.

DETAILED DESCRIPTION

In the following description of embodiments of the present invention, numerous specific details are set forth in order to provide a more thorough understanding of the present invention. However, it will be apparent to one skilled in the art that the present invention may be practiced without one or more of these specific details. In other instances, well-known features have not been described in detail to avoid unnecessarily complicating the description.

Embodiments of the present invention generally relate to a "master matching index" (MMI). An MMI is an index of records or information that may be matched against queries submitted from across a, community of entities needing information of the type contained in the MMI. The community of entities coupled to a particular MMI is herein referred to as an "MMI-based system [or network]." In one or more embodiments, an MMI-based network (or system) and method allows different entities to access a central MMI via matching management specific to each of the entities. In other words, an entity in the network may tune its matching algorithm(s) for improved matching accuracy without affecting the matching accuracy of other entities in the network.

It is noted that the scope of the present invention is not limited to matching patient records as is done with an entity-specific MPI. Rather, the principles of the present invention are equally applicable to any type of matching index. For example, an MMI in accordance with one or more embodiments may contain patient records as is done with an MPI. In one or more other embodiments, an MMI may contain information relating to physicians. For example, such a master matching index may match against name, Drug Enforcement Administration (DEA) number, and/or type. Further, in one or more embodiments, an MMI may contain information relating to insurance plans. For example, such an MMI may match against plan number and/or address for submission of insurance claims. Further, in one or more embodiments, an MMI may contain information relating to pharmacies. For example, such an MMI may match queries against addresses, phone numbers, and/or type. Further, in one or more embodiments, an MMI may contain information relating to veterinary care. For example, such an MMI may match queries against animal records (e.g., state tag number, last known home address). Further, in one or more embodiments, an MMI may contain information relating to product inventory. For example, such an MMI may contain information relating to product weight, cost, type, and/or use. Thus, although one or more embodiments are described below with reference to matching patient records, it is to be understood that any type of MMI may be used similarly, at least with respect to the distributive, matching, and process flow aspects described herein.

Figure 1:
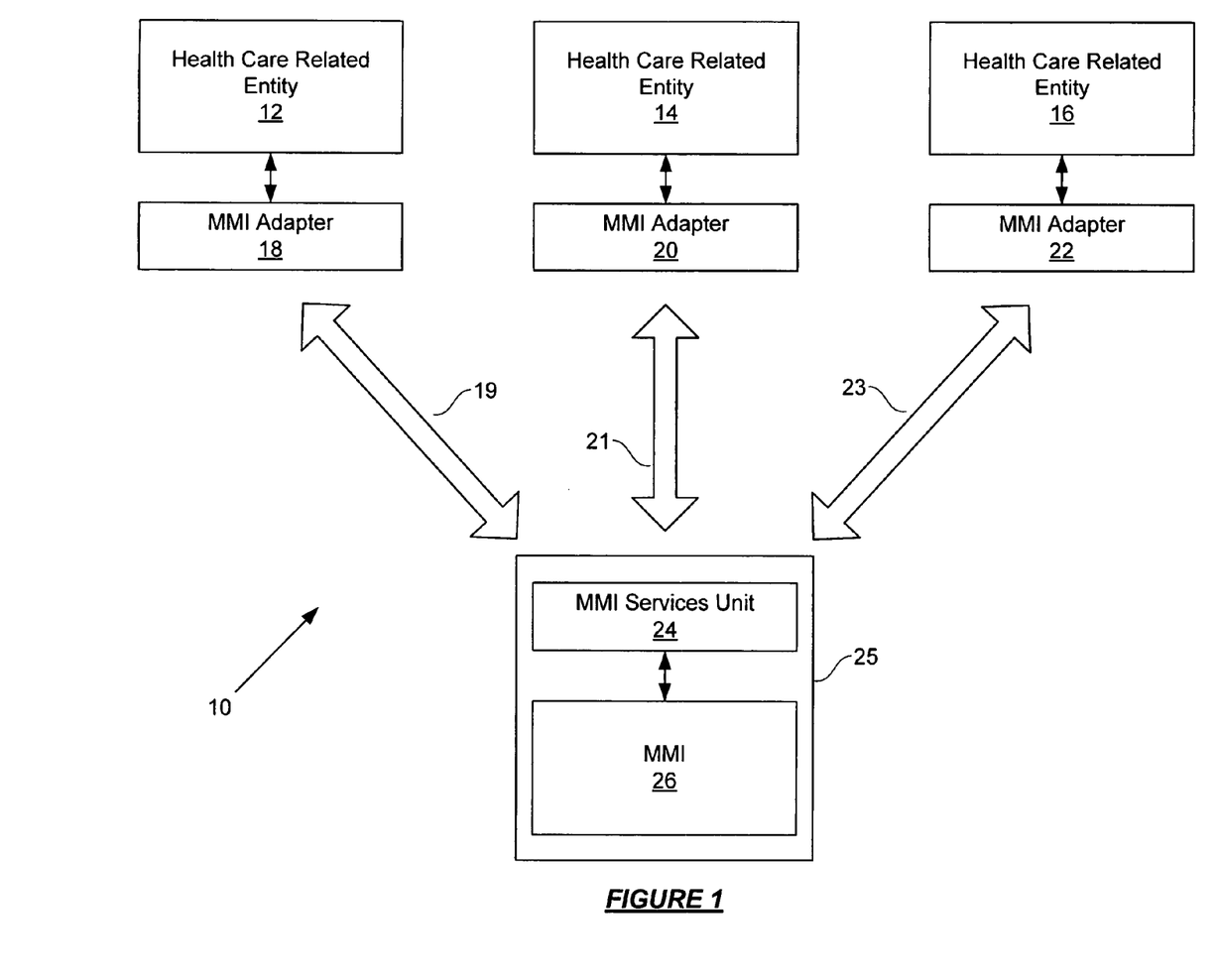
FIG. 1 shows a block diagram of an MPI-based network in accordance with an embodiment of the present invention.

FIG. 1 shows an MMI-based system 10 in accordance with an embodiment of the present invention. System 10 includes separate health care related entities 12, 14, 16. For example, one or more of health care related entities 12, 14, 16 may be a hospital, a specific department within a hospital (e.g., admissions, laboratory, radiology), a clinic, a physician's office, a pharmacy, a health insurance company, a health care organization (e.g., a health maintenance organization (HMO)), or a hospital-associated research lab.

Further, system 10 may be a local area network (LAN) (e.g., an enterprise network) or a wide area network (WAN) (e.g., the Internet). Further still, system 10 may be formed of links using technologies such as radio communication, cellular communication, Ethernet, 802.11 (wireless interface), an integrated services digital network (ISDN), a digital subscriber line (DSL), and/or an asynchronous transfer mode (ATM). Further still, networking protocols used on the system 10 may include multiprotocol label switching (MPLS), a transmission control protocol/Internet protocol (TCP/IP), a User Datagram Protocol (UDP), a hypertext transport protocol (HTTP), a simple mail transfer protocol (SMTP), a secure file transfer protocol (SFTP), and/or a file transfer protocol (FTP). Data exchanged over the system 10 may be represented using technologies and/or formats such as a hypertext markup language (HTML), an extensible markup language (XML), a simple object access protocol (SOAP), a binary file, and/or a text file. To facilitate transmission, data may be encoded in a variety of formats such as multipurpose internet email extensions (MIME) and/or a positional numeral system such as Base64. Moreover, some or all of the links across the system 10 may be encrypted using encryption technologies such as a secure sockets layer (SSL), a secure hypertext transport protocol (HTTPS), and/or a virtual private network (VPN). Regardless of whether the network links are secured, data may be encrypted using symmetric key algorithms such as, for example, AES, Blowfish, TwoFish, Serpent, or RC4, or public key techniques like Diffie-Hellman, DSS, ElGamal, and RSA. Further, in one or more embodiments, communication over the system 10 may be based on custom and/or dedicated means instead of, or in combination with, the technologies described above.

Respectively associated with each of health care related entities 12, 14, 16 in system 10 is a distributed MMI adapter 18, 20, 22. Distributed MMI adapters 18, 20, 22 (further described below with reference to FIG. 2) serve, for example, as interfaces accessible to health care related entities 12, 14, 16. Those skilled in the art will note that while a distributed MMI adapter and its associated health care related entity may reside on the same system, this need not always be the case. For example, in one or more embodiments, the distributed MMI adapter may be provided as a remote interface to the associated health care related entity.

In general, health care related entities 12, 14, 16 may access its respective distributed MMI adapter 18, 20, 22 using personal computers (e.g., laptops, desktops) having an operating system platform using Windows by Microsoft Corporation, MacOS by Apple Computer, Inc., Linux, and/or UNIX. Further, in one or more embodiments, one or more of health care related entities 12, 14, 16 may access its respective distributed MMI adapter 18, 20, 22 using other network-enabled electronic devices such as cellular telephones, personal digital assistants (PDAs), or portable e-mail devices.

Each distributed MMI adapter 18, 20, 22 is operatively connected over network connections 19, 21, 23 (e.g., the Internet, direct connection, local area network (LAN), VPN) to a database 25. The database 25, at least in part, contains an MMI services unit 24 for handling communications from/to each of the distributed MMI adapters 18, 20, 22. MMI services unit 24 (further described below with reference to FIG. 3) interfaces with an MMI 26 to perform patient matching dependent on a query from one of health care related entities 12, 14, 16 as sent from its respective distributed MMI adapter 18, 20, 22.

Accordingly, in general, a health care related entity 12, 14, or 16 needing to locate a particular patient record submits a query to its respective distributed MMI adapter 18, 20, 22. The query is embodied in a "thread" configured by the respective distributed MMI adapter 18, 20, 22, where the thread is communicated to MMI services unit 24. As used herein, a "thread" is a set of instructions awaiting execution. Thus, when one of the health care related entities 12, 14, 16 submits a query for a patient record, the query is actually sent as a set of instructions describing how and what MMI services unit 24 should look for in MMI 26.

Using MMI services unit 24, the query embodied in the thread is matched against patient records in MMI 26. The matching algorithm (or matching "scenario") used to perform the patient matching may be dictated by the thread itself In other words, the thread may contain the "logic" by which patient matching for a particular health care related entity 12, 14, 16 is to be performed (further described below with reference to FIG. 4). Such logic may be particular to the distributed MMI adapter that initiated the thread.

Thus, for example, using system 10 shown in FIG. 1, when a hospital sees a new patient, the hospital may send a query to system 10 via its distributed MMI adapter. MMI services unit 24 and MMI 26 may then use matching logic specific to the hospital to determine if the submitted patient data matches any patient records. Further, in one or more embodiments, if a match is found, the hospital may then query system 10 to obtain records from any node (a "node" refers to a combination of a health care related entity and its associated distributed MMI adapter) in system 10 that has data for the new patient. If a match is not found, other networks may be queried for the new patient's records.

In another example, using system 10 shown in FIG. 1, a physician at a clinic seeing a new patient may send a query directly through an Internet browser or web-based application using a computer system in her/her office. The patient query may then be matched against records in MMI 26. If there is a match, information from the nodes that have the patient's information may be returned to the source of the query, which, in this case, is the physician.

It is noted that the type of information submitted in a query to MMI services unit 24 may widely vary. For example, in one or more embodiments, biometric information (e.g., fingerprints, retinal scans) may be submitted as part of a query for matching. In another example, physical characteristic information (e.g., tattoo locations, scar locations, previous wound locations, dental prints, x-rays) may be submitted as part of a query for matching. In another example, identity information (e.g., name, social security number, address) may be submitted as part of a query for matching. For MMIs used for matching records other than patient records, query information may includes, for example, phone numbers, addresses, federal/state/local license or identification numbers, product weight information, product cost information, and insurance numbers.

Figure 2:
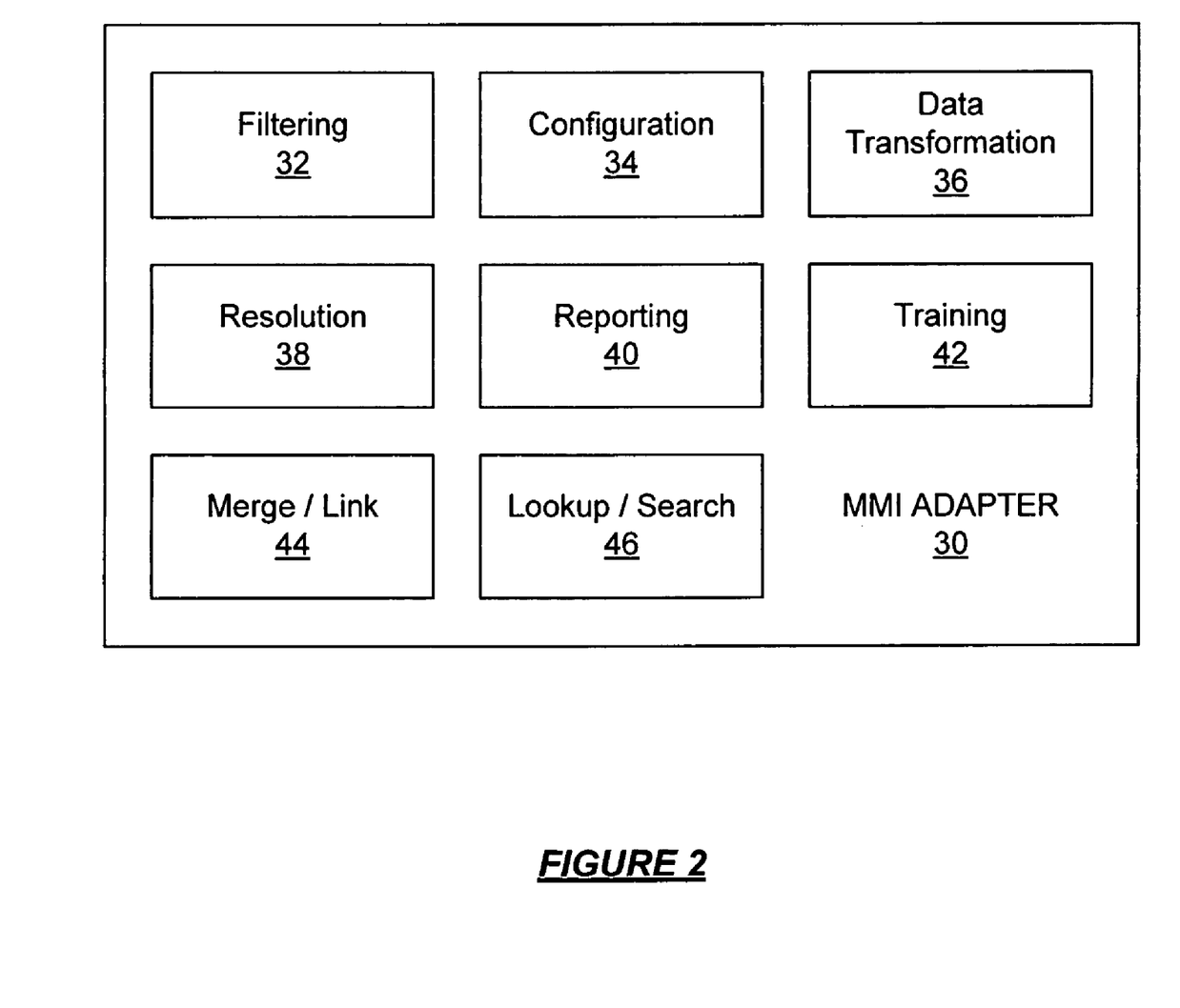
FIG. 2 shows a block diagram distributed MPI adapter in accordance with an embodiment of the present invention.

FIG. 2 shows a distributed MMI adapter 30 in accordance with an embodiment of the present invention. Distributed MMI adapter 30 shown in FIG. 2 is representative of MMI adapters 18, 20, 22 shown in FIG. 1. Still referring to FIG. 2, distributed MMI adapter 30 is accessible to an "associated" health care related entity (e.g., health care related entities 12, 14, or 16) and has a plurality of modules, each of which are described immediately below. As used herein, a "module" refers to any program logic or functionality implemented in software and/or hardware.

A filtering module 32 defines how data from an associated health care related entity is to be matched against records managed and stored by MMI services unit 24 and MMI 26. In other words, filtering module 32 specifies the algorithms or "rules" by which incoming data from the associated health care related entity is matched against patient records in MMI 26.

Distributed MMI adapter 30 may also include a configuration module 34. The configuration module 34 enables a user at an associated health care related entity to configure use of distributed MMI adapter 30. For example, using the configuration module 34, a user interface (UI) by which distributed MMI adapter 30 is accessed may be reconfigured in view of certain preferences and/or changes.

Further, distributed MMI adapter 30 may include a data transformation module 36. Data transformation module 36 may be used to transform/translate incoming data from an associated health care related entity to a data format specified or otherwise accurately recognizable by MMI services unit 24. For example, in a case where the associated health care entity stores dates in month/day/year format and MMI services unit 24 manages dates in day/month/year format, data transformation module 36 may perform or enable the functions to perform the proper date format conversion between the associated health care related entity and MMI services unit 24. Further, in another example, information specified with dashes (e.g., insurance identifies, social security numbers) may be converted by data transformation module 36 to a format without dashes (and vice-versa) depending on how data is stored in MMI 26.

Moreover, distributed MMI adapter 30 may include a resolution module 38. Resolution module 38 may be used to resolve competing returned matches. For example, if MMI services unit 24 is unable to automatically match a patient against records in MMI 26, multiple possible matches may be returned to distributed MMI adapter 30, in which case, resolution module 38 may be used to select one of the returned possible matches. In one or more embodiments, resolution module 38 may be manually used by a user to resolve a mismatch or multiple returned matches. Further, in one or more embodiments, resolution module 38 may be configured to automatically resolve a mismatch or multiple returned matches based on some predetermined logic.

Distributed MMI adapter 30 may also include a reporting module 40. Reporting module 40 may be used to generate reports regarding patient matching. For example, reporting module 40 may be used to generate or display a report indicating a percentage of successful matches. Further, in one or more embodiments, reporting module 40 may generate or display a report indicating what percentage of matching queries are having to be manually resolved (using, for example, resolution module 38).

Moreover, reports generated by reporting module 40 may be used to adjust filtering module 32. For example, if reporting module 40 indicates that 20% of matching queries are having to be manually resolved, filtering module 32 may be adjusted in a way so as to reduce the rate at which queries have to be manually resolved. Those skilled in the art will note that such adjustment may affect other aspects of patient matching via distributed MMI adapter 30. However, it is this constant "tweaking" of the algorithms/rules in filtering module 32 that may result in optimal or substantially optimal patient matching for the associated health care related entity.

Further, distributed MMI adapter 30 may include a training module 42. Training module 42 may be used for the initial generation of the algorithms/rules in filtering module 32. This may be accomplished by using performing patient matching with known sample data (representing data from the associated health care related entity). For example, sample data representing 10 known patients may be patient matched, and then, using reporting module 40, a determination may be made for generating or adjusting algorithms/rules in filtering module 32 to improve matching accuracy. Thus, in general, such "training" essentially comprises a feedback loop involving feeding sample data and testing patient matching results to adjust filtering module 32. Further, in one or more embodiments, the sample data may be periodically or regularly changed so as to test different algorithms/rules in filtering module 32. Further still, in one or more embodiments, the algorithms/rules in filtering module 32 may be adjusted, whereupon sample data is patient matched to aid in determining which algorithms/rules result in a desired level of patient matching.

Moreover, distributed MMI adapter 30 may include a merge/link module 44. Merge/link module 44 may be used to merge or link multiple returned patient records, so that for subsequent queries with the same data, a single patient record is returned to the associate health care related entity.

Distributed MMI adapter 30 may also include a lookup/search module 46. Lookup/search module 46 is used to enable a user to query data in a particular manner. For example, the lookup/search module 46 may cause various search options to be presented to the associated health care related entity for performing patient matching.

As described above with reference to FIG. 2, distributed MMI adapter 30 includes a plurality of modules 32, 34, 36, 38, 40, 42, 44, 46. However, in one or more embodiments, one or more of modules 32, 34, 36, 38, 40, 42, 44, 46 may not be present or may otherwise not be used. Further, in one or more embodiments, distributed MMI adapter 30 may have a different number and/or types of modules than that shown in FIG. 2. Further still, those skilled in the art will note that the modules 32, 34, 36, 38, 40, 42, 44, 46 may reside on a single system or over a plurality of systems, either remotely or locally connected.

Figure 3:
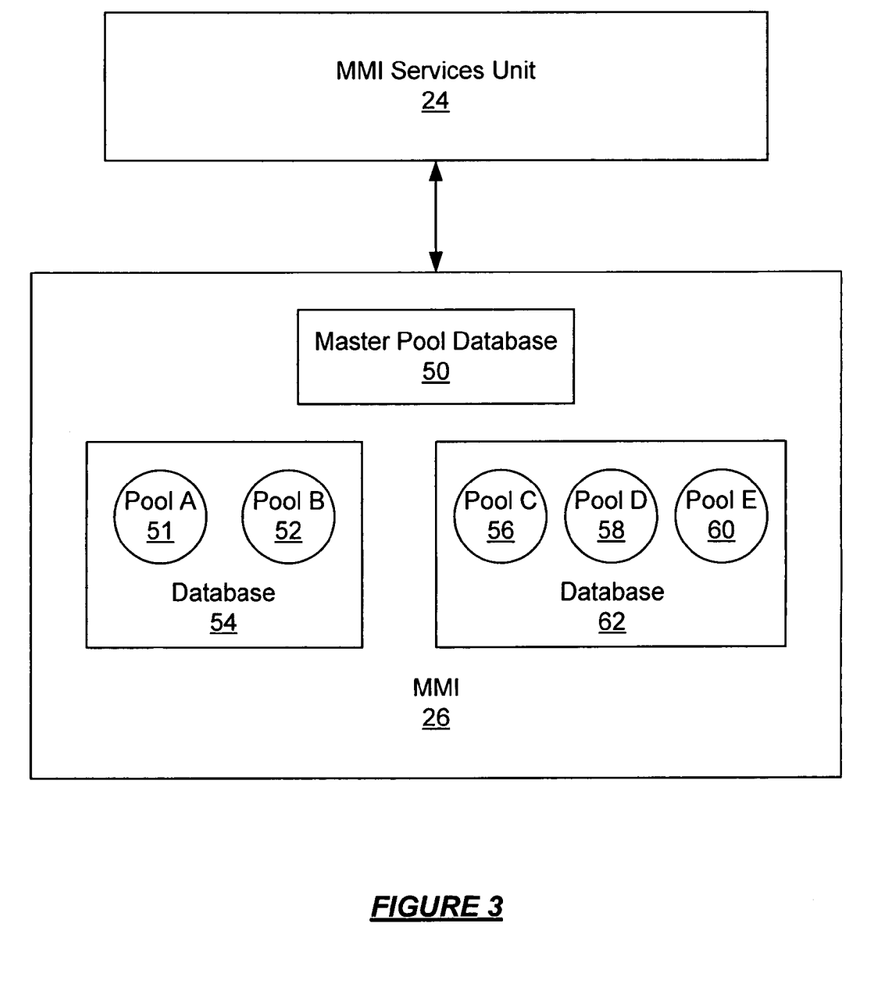
FIG. 3 shows a MMI unit in accordance with an embodiment of the present invention.

FIG. 3 shows MMI services unit 24 and MMI 26. MMI 26 includes a master pool database 50 and a plurality of pools 51, 52, 56, 58, 60 distributed across databases 54, 62. As used herein, a "pool" is a collection of entities and associated data elements. An entity may be, for example, a patient, a health care provider, or an insurance plan. A pool contains (i) one type of entity and (ii) a definition of the data elements that may be stored for an entity in the pool. For example, a patient pool may have the following data elements for each patient entity stored in the pool: first name; middle name; last name; medical record number; gender; and date of birth.

Each pool may have one or more threads. As described above with reference to FIG. 1, a thread is a "window" into the pool using one or more matching scenarios. Those skilled in the art will note that application program interfaces (APIs) that expose matching functions may require the caller to indicate which thread they are using, so as to enable MMI services unit 24 to determine which pool and which matching scenarios to use. Further, those skilled in the art will note that the ability to use multiple threads in one pool allows for the tuning of different matching scenarios for different sources of data while the pool is simultaneously matched against by the multiple threads. Further still, a pool may be "active" or "inactive"; an attempted match against an inactive pool may return an error.

As described above with reference to FIG. 1, a matching scenario defines how patients should be matched in a pool. A matching scenario may contain one or more matching methods in a sequence. The matching methods may be tried in order until a match is found. If all the matching methods have been exhausted and no match is found, MMI services unit 24 may determine that the queried entity is new to the pool.

Various different matching methods may be supported in one or more embodiments. For example, a deterministic matching method may be supported. The deterministic matching method may involve a matrix of cases, an example of which is shown below.

| First Name | Last Name | MRN | SSN | Date of Birth | Gender |
|---|---|---|---|---|---|
| Exact Match | Exact Match | Exact Match | | | |
| | | Exact Match | Exact Match | Exact Match | |
| Exact Match | Exact Match | | | Exact Match | |
| | Soundex Match | | Exact Match | Digit Sum Match | Exact Match |

In the matrix shown above, each row may be referred to as a "match case," and each cell in the matrix may be referred to as a "match operator." If any of the match cases matches, the deterministic matching method matches. If no row in the matrix matches, the deterministic method does not match. Further, various types of match operators may be supported, including, for example, exact matches ("Exact Match"), matches with spelling variations ("Soundex Match"), phonetic matches ("NYSIIS Match"), matches calculated using the sum of digits ("Digit Sum Match"), or matches that check for transposed digits using a checksum algorithm.

Further, for example, in one or more embodiments, a probabilistic matching method may be supported. The probabilistic matching method may involve a set of cases, each with one or more mutually exclusive outcomes. An example of a set of cases usable by a probabilistic matching method is shown below.

| Case | Outcome | Description | Score |
|---|---|---|---|
| Name | N1 | First and Last name exact match | 65 |
| | N2 | Last name matches, first name SOUNDEX or NYSIIS match | 50 |
| | N3 | Last and first names SOUNDEX or NYSIIS | 40 |
| | N4 | Other name configuration | −65 |
| Date of Birth | D1 | Matches | 40 |
| | D2 | Sum of digits matches | 20 |
| | D3 | Does not match | −40 |
| SSN | S1 | Matches | 80 |
| | S2 | Any of the following are true: All digits are the same (999-99-9999) Digits are ascending (123-45-6789) Digits are descending (987-65-4321) | 0 |
| | S3 | Other SSN configuration | −80 |
| | | Total Score Required to Match | 100 |

Each case may be evaluated and its resulting score may be added to a running tally. If a final tally is greater than a given threshold, the probabilistic matching method matches; otherwise, it does not. Further, those skilled in the art will note that in a probabilistic matching method, a particular case may include more than one data element.

Still referring to FIG. 3, MMI services unit 24 and MMI 26 may have various features, at least some of which are now described.

Matching API

MMI services unit 24 may expose an API that provides access to matching functions. Such an API may enable the following: pool, thread, scenario, and case management, including adding, editing, viewing, updating, and deleting; matching functionality to match on a given thread; match/add functionality to match on a given thread and add the entity if no match is found; query functionality for searching and displaying data from a particular pool; and entity management for linking and unlinking entities in a pool, editing data associated with an entity, and forcing two entities to never match.

Matching Pools

Further, in one or more embodiments, MMI services unit 24 may support matching pools across databases 54, 62. Master pool database 50 may be used to map incoming threads to the appropriate pool. Moreover, in one or more embodiments, MMI services unit 24 may support matching pools in a single database.

Match Threads

Further still, in one or more embodiments, a thread may be connected to exactly one pool. The thread may have a primary matching scenario, a second matching scenario for searching potential duplicates (described below), and a third matching scenario for auto-merging (described below).

Matching Scenarios

For each pool, a user may create any number of matching scenarios. MMI services unit 24 and MMI 26 may support multiple match scenarios per pool—one that performs the actual match and a secondary one that may be used to generate "potential" duplicates that a user may need to review. Those skilled in the art will note that the secondary match scenario may be used for real-time potential duplicate checking.

Pool Viewer/Search

In one or more embodiments, a user may search a pool and view and edit data associated with a particular entity in the pool. Further, the user may create a new entity or delete (or mark for deletion) an outdated or old entity. Further still, in one or more embodiments, additions/edits to data in the pool may be run against a match thread to inform the user if a duplicate entity is being created.

Entity Specific Demographics

In one or more embodiments, when defining a pool of data, an administrator may select one or more data elements that have a copy of that data element stored for each contributing health care related entity. For example, the administrator may create a pool which has patient name and address data elements and configure the address elements to be stored per each health care related entity. Thus, each entity in the pool has one name, which is shared among all contributing health care related entities, but the address fields are stored once per contributing health care related entity. When a particular contributing health care related entity executes a match or asks for the data for a particular entity in the pool, the data elements associated with that contributing health care related entity are returned, as well as the shared data elements. Accordingly, in general, matching may occur against a record set for a specific health care related entity.

Duplicates Log

Further, in one or more embodiments, when MMI 26 runs a match on a particular thread and finds more than one patient that matches, MMI services unit 24 may create a new entity in MMI 26 and adds all of the matching patients to a "duplicates" log. A merging tool may then traverse the duplicates log. A simple report may then output current duplicates in the duplicate log. The log may also be traversed online using the merging tool.

Potential Matches Log

Further, in one or more embodiments, MMI services unit 24 may maintain a "potential matches" log. For example, such a log may be created when secondary matching scenarios have been configured on one or more threads.

Auto-Merge

In one or more embodiments, when a successful match is found using a primary matching scenario on a thread, MMI services unit 24 may take data from the matched entity and run that data against an auto-merge matching scenario. If two or more matches are found, MMI services unit 24 may merge the found matches.

Scenario Report

In one or more embodiments, a report may be generated for allowing a user to choose an arbitrary scenario in the pool (whether it is "hooked" to a thread or not) and find any duplicates in the pool according to that scenario. Such a matching scenario may involve, for example, comparing every entity in a pool to every other entity in the pool.

Statistics

Further, in one or more embodiments, MMI services unit 24 may keep a pool of statistics for each matching pool. Statistical information may relate to, for example, the number of entities in the pool per week over the past year, how many requests processed per hour per pool over the last month, etc. Further still, MMI services unit 24 may keep statistics on duplicates and potential matches.

Pool Management

In one or more embodiments, MMI services unit 24 may create and define pools. Further, MMI services unit 24 may define the types of data elements allowed in a particular pool.

Thread Management

In one or more embodiments, MMI services unit 24 may create, edit, and/or delete threads in any pool. Further, MMI services unit 24 may attach primary and secondary matching scenarios to a thread.

Scenario Management

In one or more embodiments, MMI services unit 24 may create, edit, and/or delete matching scenarios in any pool. Further, MMI services unit 24 may create, edit, and/or delete global matching scenarios, i.e., matching scenarios common to all pools managed by MMI services unit 24. Further still, MMI services unit 24 may create, edit, and/or delete, for example, deterministic and probabilistic matching methods and their associated cases, operators, and outcomes.

Thread Testing

In one or more embodiments, MMI services unit 24 may allow a user to select a thread and manually enter values for any data element to which the thread is attached. The user may then initiate a search on that thread and determine whether there was a primary or secondary match or no match at all.

Entity Link/Unlink

In one or more embodiments, MMI services unit 24 may allow a user to work either the duplicates log or the potential matches log for a particular pool and merge patients (as well as flagging two potential matches as being different), so they are not suggested as potential matches again. Further, MMI services unit 24 may allow a user to search a pool and find any two entities and merge them or flag them as different. Further still, in one or more embodiments, when two patients are merged, MMI services unit 24 may keep the "old" patient around and link it to the new patient.

Figure 4:
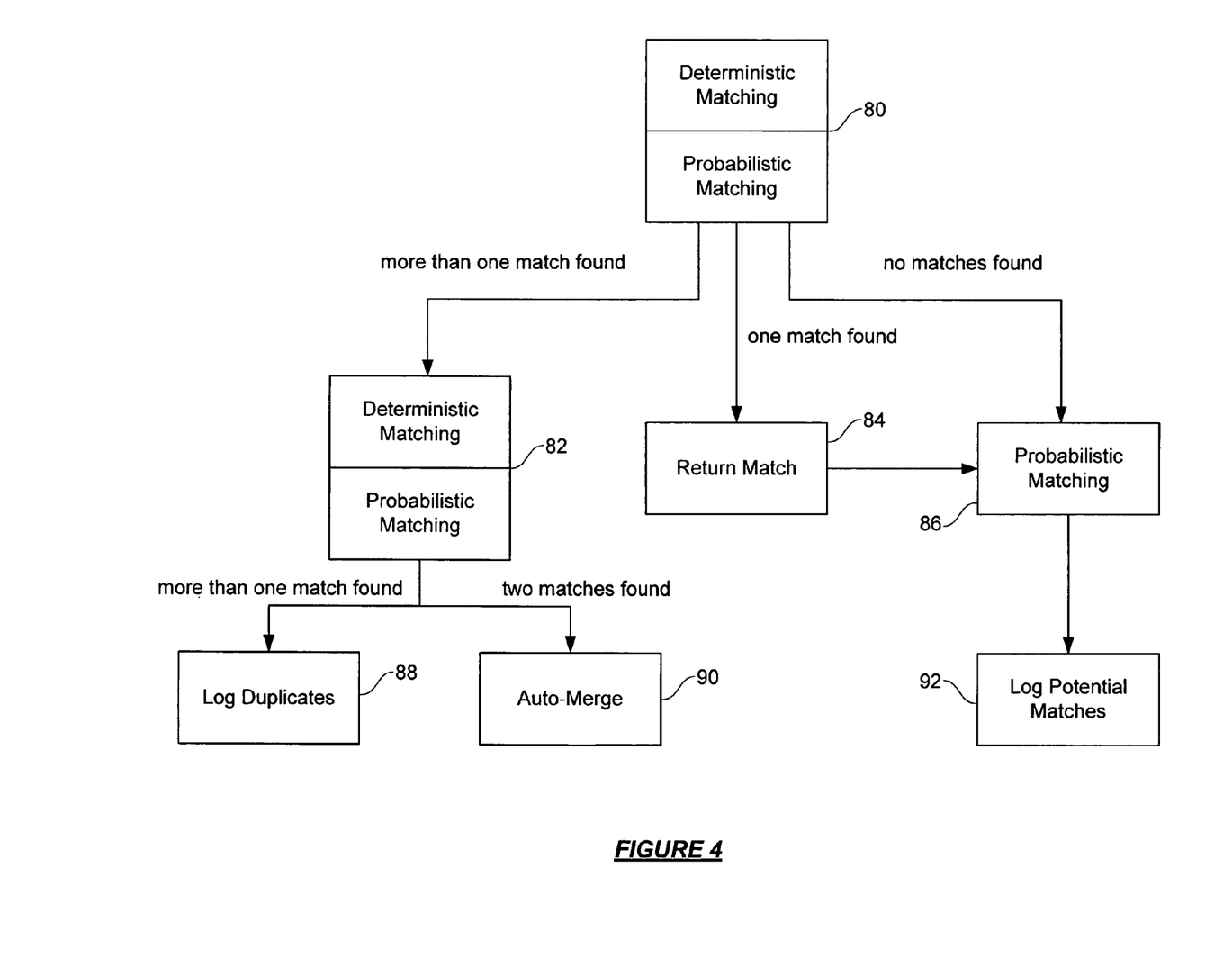
FIG. 4 shows a flow process of a thread in accordance with an embodiment of the present invention.

FIG. 4 shows a flow process of a thread in accordance with an embodiment of the present invention. The thread may initially perform a sequence 80 of deterministic matching followed by probabilistic matching. If only one match is found, the match is returned 84. Thereafter, or if no matches are found, a probabilistic matching may be performed 86, whereafter potential matches may be logged 92.

If more than one match is found when performing the initial sequence 80 of deterministic matching followed by probabilistic matching, another sequence 82 of deterministic matching followed by probabilistic matching may be performed. As a result, if two matches are found, the results may be auto-merged 90. Otherwise, if more than one match is found, the duplicates may be logged 88.

Further, one or more embodiments of the present invention may be associated with virtually any type of computer system, including multiprocessor and multithreaded uniprocessor systems, regardless of the platform being used. For example, a networked computer system includes at least one processor (e.g., a general-purpose processor, a field-programmable gate array (FPGA), an application-specific integrated circuit (ASIC), a graphics processor), associated memory, a storage device, and numerous other elements and functionalities typical of modern computer systems. The networked computer system may also include input means (e.g., a keyboard, a mouse) and output means (e.g., a monitor). The networked computer system may be connected to a LAN or a WAN via a network interface connection. Those skilled in the art will appreciate that these input and output means may take other forms. Further, those skilled in the art will appreciate that one or more elements of the networked computer system may be remotely located and connected to the other elements over a network. Further, software instructions to perform one or more embodiments of the present invention may be stored on a computer-readable medium such as a compact disc (CD), a diskette, a tape, a file, a hard drive, or any other computer-readable storage device.

Advantages of the present invention may include one or more of the following. In one or more embodiments, an MMI-based network may be used for record matching, where matching management for the MMI is specifically distributed across entities in the network.

In one or more embodiments, an MMI-based network may allow for matching algorithm adjustments for one entity in the network without affecting matching algorithms used by other entities in the network.

In one or more embodiments, an improved MMI-based network may allow for reliable access to the MMI without compromise otherwise necessary when using a non-distributed MMI architecture.

While the invention has been described with respect to a limited number of embodiments, those skilled in the art, having benefit of the above description, will appreciate that other embodiments may be devised which do not depart from the scope of the present invention as described herein. Accordingly, the scope of the present invention should be limited only by the appended claims.

What is claimed is:

1. A system for accessing stored entities comprising:
a master matching index stored on a database including a collection of entities and data elements associated with each entity, at least one of the data elements having a first value associated with a first secondary system and a second value associated with a second secondary system;
a services unit operatively coupled to the master matching index and arranged to control access to the master matching index;
a first adapter stored on a first memory and executable on a first processor, the first adapter operatively coupled to the services unit and to the first secondary system, the first adapter comprising a first training module for testing a first matching algorithm with known data and adjusting the first matching algorithm based on results of a test of the first matching algorithm, the first adapter receiving a first query from the first secondary system identifying a first plurality of data elements specifying a first entity that includes the at least one of the data elements having the first value, transforming the first query into a data format that is recognized by the services unit and generating a first thread from the first query, the first thread comprising:
a first set of instructions for accessing the master matching index,
the first plurality of data elements and
the first matching algorithm associated with the first secondary system including a first set of rules for comparing the first plurality of data elements in the first thread to entities in the master matching index, the first set of rules including at least one of a probabilistic matching rule and a deterministic matching rule,
a second adapter operatively coupled to the services unit and to the second secondary system, the second adapter comprising a second training module for testing a second matching algorithm with known data and adjusting the second matching algorithm based on results of a test of the second matching algorithm, the second adapter receiving a second query from the second secondary system identifying a second plurality of data elements specifying a second entity that includes the at least one of the data elements having the second value, transforming the second query into the data format that is recognized by the services unit and generating a second thread from the second query, the second thread comprising:
a second set of instructions for accessing the master matching index,
the second plurality of data elements and
the second matching algorithm associated with the second secondary system including a second set of rules for comparing the second plurality of data elements in the second thread to entities in the master matching index, the second set of rules including at least one of the probabilistic matching rule and the deterministic matching rule, and
wherein the services unit receives the first thread from the first adapter, compares the first plurality of data elements from the first thread with entities in the master matching index using the first set of rules included in the first matching algorithm and retrieves an entity associated with data elements satisfying the first matching algorithm from the master matching index.

2. The system of claim 1, wherein the first and second adapters are remote from at least one of the services unit and the master matching index.

3. The system of claim 1, wherein the first adapter comprises:
a filtering module arranged to specify the first matching algorithm.

4. The system of claim 1, wherein the probabilistic matching rule describes a set of cases, each with one or more mutually exclusive outcomes, and the deterministic matching rule describes one or more match cases and match types.

5. The system of claim 1, wherein the first adapter comprises:
a configuration module arranged to at least one of configure and render a user interface accessible to the first secondary system.

6. The system of claim 1, wherein the first adapter comprises:
a data transformation module arranged to convert data in a format of the first secondary system to a format of the master matching index.

7. The system of claim 1, wherein the first adapter comprises:
a resolution module arranged to resolve multiple records returned by at least one of the services unit and the master matching index.

8. The system of claim 1, wherein the first adapter comprises:
a reporting module arranged to indicate a statistic relating to queries by the first secondary system in the master matching index.

9. The system of claim 1, wherein the first training module generates the first matching algorithm based on results of a matching accuracy with known data.

10. The system of claim 1, wherein the first training module compares results of the first matching algorithm with results of the second matching algorithm and adjusts the first matching algorithm based on the comparison.

11. The system of claim 1, wherein the first adapter is operatively coupled to the services unit at least in part over the Internet.

12. The system of claim 1, wherein the master matching index comprises at least one pool for storing an entity and associated data elements.

13. The system of claim 1, wherein the first secondary system comprises at least one of a hospital, a medical group, an insurance provider, a health care provider, a veterinary care-related entity, a pharmacy, and a private clinic.

14. The system of claim 1, wherein the master matching index comprises information relating to at least one of patients, physicians, insurance plans, pharmacies, animals, and product inventory.

15. A method, comprising:
accessing a first user interface supported by a first adapter having a first processor, the first adaptor coupled to a master matching index stored on a database including a collection of entities and data elements associated with each entity, at least one of the data elements having a first value associated with a first secondary system and a second value associated with a second secondary system;
testing a first matching algorithm with known data;
adjusting the first matching algorithm based on results of a test of the first matching algorithm;
specifying a first query identifying a first plurality of data elements associated with a first record via the first user interface;
transforming the first query into a data format that is recognized by a services unit;
generating with the first processor, a first thread from the first query via the first adapter, the first thread comprising a first set of data elements, a first set of instructions for accessing the master matching index and the first matching algorithm associated with the first secondary system, the first matching algorithm including a first set of rules for comparing the first plurality of data elements in the first thread to entities in the master matching index, the first set of rules including at least one of a probabilistic rule and a deterministic matching rule;
comparing, using the services unit coupled to the master matching index, the first set of data elements included in the first thread against different entities in the master matching index according to the first matching algorithm specified in the first thread generated by the first adapter;
responsive to a first entity in the master matching index satisfying the first matching algorithm associated with the first secondary system, presenting the first entity from the master matching index satisfying the first matching algorithm using the first user interface, the first entity including the at least one of the data elements having the first value;
accessing a second user interface supported by a second adapter coupled to the master matching index;
testing a second matching algorithm with known data;
adjusting the second matching algorithm based on results of a test of the second matching algorithm;
specifying a second query identifying a plurality of data elements associated with a second record via the second user interface;
transforming the second query into the data format that is recognized by the services unit;
generating a second thread from the query via the second adapter, the second thread comprising a second set of data elements, a second set of instructions for accessing the master matching index and the second matching algorithm associated with the second secondary system, the second matching algorithm including a second set of rules for comparing data elements in the second thread to entities in the master matching index, the second set of rules including at least one of the probabilistic matching rule and the deterministic matching rule; and
responsive to a second entity in the master matching index satisfying the second matching algorithm associated with the second secondary system, presenting the second entity from the master matching index satisfying the second matching algorithm using the second user interface, the second entity including the at least one of the data elements having the second value.

16. The method of claim 15, further comprising configuring the first user interface.

17. The method of claim 15, further comprising resolving multiple records returned in response to the first query.

18. The method of claim 15, further comprising generating a report indicating at least one statistic relating to a record returned in response to the first query.

19. A method executable on a processor for matching information in a master matching index stored on a database, comprising:
testing a first matching algorithm with known data;
adjusting the first matching algorithm based on results of a test of the first matching algorithm;
receiving a first thread comprising a first plurality of data elements, a first set of instructions for accessing the master matching index and the first matching algorithm associated with a first secondary system, the first matching algorithm including a first set of rules for comparing data elements in the first thread to entities in the master matching index from the first secondary system via a first adapter, the first set of rules including at least one of a probabilistic matching rule and a deterministic matching rule, the master matching index stored on the database including the entities and data elements associated with each entity, at least one of the data elements having a first value associated with the first secondary system and a second value associated with a second secondary system;

comparing with the processor, using a services unit, the first plurality of data elements included in the first thread to data elements associated with a first record indexed in the master matching index according to the first matching algorithm associated with the first secondary system included in the received first thread specified in the first adapter, the first record including the at least one of the data elements having the second value;

testing a second matching algorithm with known data;

adjusting the second matching algorithm based on results of a test of the second matching algorithm;

receiving a second thread comprising a second plurality of data elements, a second set of instructions for accessing the master matching index and the second matching algorithm associated with the second secondary system, the second matching algorithm including a second set of rules for comparing data elements in the second thread to entities in the master matching index from the second secondary system via a second adapter, the second set of rules including at least one of the probabilistic matching rule and the deterministic matching rule; and comparing with the processor, using a services unit, the second plurality of data elements included in the second thread to data elements associated with a second record indexed in the master matching index according to the second matching algorithm associated with the second secondary system included in the received second thread specified in the second adapter, the second record including the at least one of the data elements having the second value.

20. The method of claim 19, further comprising returning the first record if a single match is found in response to comparing the first plurality of data elements included in the first thread to data elements associated with the first record.

21. The method of claim 19, further comprising returning at least one potential match if the first record is not found in response to comparing the first plurality of data elements included in the first thread to data elements associated with the first record.

22. The method of claim 19, further comprising merging records if at least two matches are found in response to comparing the first plurality of data elements included in the first thread to data elements associated with the first record.

23. The method of claim 19, further comprising recording duplicate matches if more than one match is found in response to comparing the first plurality of data elements included in the first thread to data elements associated with the first record.

24. The method of claim 19, wherein the rules for comparing the first set of data elements in the first thread to entities in the master matching index comprise at least one of:

deterministically matching the data elements in the first thread using one or more match cases and one or more match types; and probabilistically matching the data elements in the first thread using a set of cases, each case with one or more mutually exclusive outcomes.

25. The method of claim 19, further comprising allowing a user to modify data stored in the master matching index.

26. The method of claim 19, further comprising returning the first record including the at least one of the data elements having the first value in response to comparing the first plurality of data elements included in the first thread to data elements associated with the first record.

27. A method for passing information over a network having at least first and second health care related entities, comprising:

storing patient information in a master patient index (MPI) on a database including patients and data elements associated with each patient, at least one of the data elements having a first value associated with the first health care related entity and a second value associated with the second health care related entity;

testing, by a first adapter, a first MPI matching algorithm with known data;

adjusting, by the first adapter, the first MPI matching algorithm based on results of a test of the first MPI matching algorithm;

receiving, at the first adapter operatively coupled to the MPI, a first query from the first health care related entity for a first patient in the MPI, the first patient including the at least one of the data elements having the first value;

selecting, by the first adapter, the first MPI matching algorithm for the first query that is specific to the first health care related entity, the first MPI matching algorithm including a first set of rules including at least one of a probabilistic matching rule and a deterministic matching rule;

testing, by a second adapter, a second MPI matching algorithm with known data;

adjusting, by the second adapter, the second MPI matching algorithm based on results of a test of the second MPI matching algorithm;

receiving, at the second adapter operatively coupled to the MPI, a second query from the second health care related entity for a second patient in the MPI, the second patient including the at least one of the data elements having the second value;

selecting, by the second adapter, the second MPI matching algorithm for the second query that is specific to the second health care related entity, the second MPI matching algorithm including a second set of rules including at least one of the probabilistic matching rule and the deterministic matching rule; and wherein performance of the first MPI matching algorithm and performance of the second MPI matching algorithm are independent of one another.

28. The system of claim 1, wherein the first and second entities are the same type.

29. The system of claim 1, wherein the first and second entities are different types.

* * * * *